United States Patent [19]

Schmidt et al.

[11] Patent Number: 4,881,542

[45] Date of Patent: Nov. 21, 1989

[54] TUBULAR FLEXIBLE PROBE FOR INTRODUCTION INTO THE TRACHEA AND, RESPECTIVELY, INTO THE BRONCHIAL SYSTEM

[76] Inventors: Christoph Schmidt, Am Kumpel 12, 5300 Bonn 1; Rudolf Schon, Im Spichelsfeld 34, 5205 St. Augustin; Jurgen Russ, Rosental 32, 5300 Bonn 1, all of Fed. Rep. of Germany

[21] Appl. No.: 27,432

[22] Filed: Mar. 18, 1987

[30] Foreign Application Priority Data

Mar. 18, 1986 [DE] Fed. Rep. of Germany ....... 3608943
Jul. 10, 1986 [WO] PCT Int'l Appl. ............ DE86/00283

[51] Int. Cl.$^4$ ............................................. A61M 16/00
[52] U.S. Cl. .................. 128/207.14; 604/43; 604/27
[58] Field of Search ..................... 128/207.14, 207.15; 604/19, 27, 28, 30, 35, 39, 40, 43, 128, 129, 165

[56] References Cited

U.S. PATENT DOCUMENTS

| | | | |
|---|---|---|---|
| 3,605,751 | 9/1971 | Gulling | 128/204.14 |
| 4,214,593 | 7/1980 | Imbruce et al. | 604/45 |
| 4,300,550 | 11/1978 | Gandi et al. | |
| 4,344,436 | 8/1982 | Kubota | 604/3 F |
| 4,364,394 | 12/1982 | Wilkinson | 604/35 |
| 4,405,313 | 9/1983 | Sisley et al. | 604/43 |
| 4,468,216 | 8/1984 | Muto | 604/43 |
| 4,508,533 | 4/1988 | Abramson | 604/35 |
| 4,676,778 | 6/1987 | Nelson, Jr. | 604/48 |

FOREIGN PATENT DOCUMENTS

| | | |
|---|---|---|
| 2736771 | 2/1978 | Fed. Rep. of Germany . |
| 2364119 | 10/1978 | Fed. Rep. of Germany . |
| 2847681 | 5/1980 | Fed. Rep. of Germany . |
| 3127249 | 6/1982 | Fed. Rep. of Germany . |
| 3327586 | 2/1984 | Fed. Rep. of Germany . |
| 3506738 | 10/1985 | Fed. Rep. of Germany . |
| 3608943 | 8/1987 | Fed. Rep. of Germany . |
| 2954308 | 12/1980 | France ................... 604/43 |
| 0808085 | 3/1981 | U.S.S.R. ................. 604/43 |
| 2032780 | 5/1980 | United Kingdom ........ 604/43 |

Primary Examiner—Max Hindenburg
Assistant Examiner—K. M. Reichle
Attorney, Agent, or Firm—Antonelli, Terry & Wands

[57] ABSTRACT

A tubular flexible probe for introduction into the trachea and, respectively, into the bronchial system, has a continuous first lumen with a connecting piece provided at the proximal inlet end for connection to a suction device and, extending therebeside, a further small lumen having a smaller diameter than the first lumen. A wall of the smaller lumen has a recess in the zone of the proximal inlet end of the probe with an elastic connecting hose being inserted with one end in the smaller lumen in the recess. For the alternating introduction of medicaments and, respectively, irrigation solution at a high exit velocity at the distal probe end through the smaller lumen and for removing secretions or the like by suction, the probe has a length of about 30–55 cm and an outer diameter of about 5–8 mm. The large first lumen has a diameter of about 3–4.5 mm, the small lumen has a diameter of about 1 to maxially 2 mm, and the two lumens extend from the proximal end up to the distal, rounded end of the probe in side-by-side relationship and in parallel to the probe axis. An attachment for a syringe is formed at the inlet end of the connecting hose.

14 Claims, 3 Drawing Sheets

TUBULAR FLEXIBLE PROBE FOR INTRODUCTION INTO THE TRACHEA AND, RESPECTIVELY, INTO THE BRONCHIAL SYSTEM

BACKGROUND OF THE INVENTION

This invention relates to a tubular flexible probe for introduction into the trachea and, respectively, into the bronchial system, containing a continuous first lumen designed for suction with a connecting piece provided at the proximal inlet end for connection to a suction device and, extending therebeside, a second lumen for the administration of media, having a smaller diameter than the first lumen for the suction removal, wherein the wall of the smaller second lumen has a recess in the zone of the proximal inlet end of the probe, wherein an elastic connecting hose is provided for the administration of media, and wherein optionally, in the distal end zone of the probe, at least one penetrating hole is arranged in a wall defining the large lumen toward the outside.

The following steps must be performed in the treatment of patients for respiration and reanimation:

(1) Introduction of irrigation solution into the tracheal and bronchial space.

(2) Suction removal of irrigation solution, mucous, secretions, blood, etc., from the tracheal and bronchial space.

(3) Respiration and, if necessary, oxygen supply.

(4) Furthermore, efforts are being made recently to provide the patient additionally with a direct and fast supply of medicaments to be introduced into the bronchial space.

Heretofore, the following devices have been utilized for the aforementioned treatment:

For steps (1) and (2):

single-lumen suction catheter, as described, for example, in DAS No. 23 64 119 (U.S. Pat. No. 3,848,604), DOS No. 14 91 652 (U.S. Pat. No. 3,375,828) or DOS No. 25 40 536.

For step (3):

double-lumen respirator tube or balloon catheter, as known, for example, from U.S. Pat. No. 4,300,550, DOS No. 28 47 681 and DOS No. 23 08 400.

For step (4):

there is not as yet a suitable device for the introduction of medicaments through the trachea directly deeply into the lung.

When using, for this purpose, the conventional, single-lumen suction catheters (see steps (1) and (2)), then there is the great disadvantage that the medicaments must be introduced only after suctioning through the single lumen. On account of the relatively large diameter of the lumen serving for suction removal of secretions and mucus, medicaments pass only with small proportions into the lung while otherwise remaining in the catheter. Efforts to introduce and distribute the medicaments entirely and deeply into and within the lung are unsuccessful. There is the further drawback that the conventional suction catheters are not equipped with attachments for fitting a syringe, which is, however, necessary for administering medicaments in the liquid form.

The conventional respirator tubes utilized for step (3) are likewise unsuitable for introducing medicaments through the trachea to deep into the lung. These known respirator tubes exhibit a relatively large diameter for the air volume and can be introduced only as far as the trachea. With a relatively short length of the respirator tubes, the introduced medicaments would be held up already on the way to the lungs. The desired introduction and distribution of medicaments to deeply into the lung is impossible.

The endotracheal respirator tube according to DOS No. 23 08 400 comprises a distal beveled, sharp-edged tip which would lead to considerable injuries to the bronchial system and therefore cannot be introduced as far as the bronchi.

In the respirator tube according to DOS No. 23 08 400, suction is also to be possible in addition to respiration; for this purpose, a hose is extended through the tube coaxially as a catheter which reduces and impedes the tube cross section. Also, the hose is loosely suspended in the large lumen of the respirator tube and protrudes from the end whereby no control can be exerted on its position. Using this respirator tube, suction can only be performed intermittently during expiration. Irrigation and simultaneous suction removal of secretions is impossible with the respirator tube according to DOS No. 23 08 400 since, with the irrigation fluid being supplied via the catheter, suction would have to be effected via the tube; in such a case, the respirator tube would adhere by suction to the bifurcation, resulting in diffuse, gravest hemorrhaging with great danger to life. The necessary respiration and, respectively, oxygen exchange can then not be performed simultaneously during irrigation and suctioning. This respirator tube thus is likewise entirely unsuitable for the introduction of medicaments deeply into the lung.

Similar conditions are encountered with the endotracheal respirator tube according to DOS No. 28 47 681 which, on account of its large diameter for air exchange (respiration), the shortness of the tube, and the beveled, sharp-edged distal end, cannot be introduced to deeply into the bronchial system and therefore is not suited for the administration of medicaments to be distributed in the lung. Insofar as the supply hoses for additional oxygen feed are arranged within the large lumen of the tube, they actually do not impede respiration and air exchange—however, suction removal of secretions is no longer possible with this tube.

The endotracheal respirator tube known from U.S. Pat. No. 4,300,550 contains a continuous, large lumen for suctioning air, the proximal end of this lumen being connected to a vacuum device. For the simultaneous feeding of oxygen, the respirator tube contains a second, smaller lumen extending therebeside, the distal end or, respectively, distal outlet openings of which are provided far upstream of the distal end of the tube so that the exiting oxygen is conducted on the outside along the distal tube region.

This endotracheal respirator tube according to U.S. Pat. No. 4,300,550 likewise proves to be unsuitable for the administration of medicaments to deeply into the lung. The large respirator lumen is not suited, because the medicaments get stuck without flow pressure; in case of the small lumen, in contrast thereto, the medicaments get caught in the outlet zone between the tube and the trachea and also do not pass on to the desired site on account of the shortness of the respirator tube.

Furthermore, double-lumen drainage catheters have become known from wound treatment, equipped with relatively large outer diameters for a high suction volume, a relatively short length, and a beveled tip, as disclosed, for example, in French Patent No. 2,454,308. In order to ensure adequate suction, these drainage catheters also exhibit additionally holes providing connection to the outside air in the proximal region of the large lumen. Such drainage catheters which, in their use, are placed and handled visually—i.e., with eye control—are completely unsuited for use in the endotracheal or endobronchial regions. Their type of structure would immediately lead to tissue damage.

The invention is based on the object of providing a probe or catheter usable for introducing medicaments in the liquid form through the trachea and, respectively, bronchi to deeply into the bronchial system and, respectively, the lung, namely in conjunction with suction removal of secretions and mucus or the like from the bronchial system.

SUMMARY OF THE INVENTION

The invention attains the posed objective by means of a tubular flexible, double-lumen probe which is designed so that it is suited for introduction into the trachea and, respectively, the bronchial system and can be used for the alternating introduction of medicaments and, respectively, irrigation solution at a high exit velocity at the distal probe end through the smaller lumen, and suctioning of secretions or the like through the large lumen. The probe according to this invention exhibits, in particular, the features that the probe has a length of about 30–55 cm, an outer diameter of about 5–8 mm, the large lumen for suctioning has a diameter of about 3–4.5 mm, and the small lumen has a diameter of about 1 to maximally 2 mm, the two lumens extend from the proximal end to the distal end of the probe in side-by-side relationship and in parallel to the probe axis, the two lumens terminate side-by-side at the distal end of the probe, the attachment at the inlet end of the connecting hose is designed as an attachment for a syringe, and the distal end of the probe is fashioned to be rounded.

The invention is based on the realization that a maximally high pressure difference is required between the ends of the lumen of the probe through which the medicaments are to be conveyed, in order to obtain a high flow rate for the deep introduction and distribution of medicaments in the liquid form into and within the lung. For this purpose, very small cross sections of the lumen are required along the lines of the invention; preferably, lumens are employed having a diameter of about 1 to 1.5 mm. In order to achieve a fine distribution at the end of the probe during exiting, it may be advantageous to widen the small lumen slightly at the distal outlet end in the form of a nozzle.

Furthermore, the probe must be suitable for flawless introduction into the bronchial system without damage to the mucous membranes and bronchi. In this connection, the experience gained with single-lumen catheters, as known for suctioning mucus and water from the lung, is used as a basis, and such probes are fashioned, according to this invention, with an additional, continuously extending lumen of such a small cross section that the deep introduction of medicaments into the lung at a high flow rate is made possible. At the same time, the entrance orifice of this small lumen is equipped with an attachment for fitting a syringe; in this context, the connecting piece can be fashioned as a separate component or integrally at the end of the connecting hose. The attachment serves herein for the attachment of a syringe for the introduction of the liquid medicaments wherein the attachment can also be equipped, for example, additionally with a closure means, such as a valve, stopper, sealing cap.

The probe according to this invention permits, in rapid succession, without any problems the alternating introduction of medicaments through the small lumen and suctioning through the large lumen. Furthermore, at the same time irrigation solution can be supplied via the small lumen and suction removal can be performed through the large lumen. The probe of this invention thus makes it possible, with a single appliance, to perform a plurality of treatments on a patient, permitting the rapid optimum caretaking for a patient in an emergency.

Thus, according to the invention, the large lumen of the probe has a cross-section still of adequate size for suctioning off mucus, and the additional smaller lumen, with the very much smaller diameter, is still sufficient for transporting the medicaments directly into the lung under high pressure buildup, and simultaneously distributing the medicaments thoroughly. Both lumens together must not exceed, with their outer diameters and wall thicknesses, the maximally permissible outer diameter of the probe since otherwise introduction into the trachea is impeded. The permissible differences in the outer diameters and the length of the probe are designed for the differing constitution of the patients, for example, children and adults.

The two lumens extend at the distal probe end axially in parallel to the probe axis so that the medicaments continue to flow with high pressure in the axial direction and penetrate deeply into the lung with a nozzle-type, fine distribution. In this connection, the lumens can terminate flush with the distal end of the probe. It is likewise possible, and advantageous in certain cases, to combine the smaller lumen still within the probe, a few millimeters upstream of the distal probe end, in parallel extension with the large lumen, and have them exit together at the distal end in a flush manner. This can be accomplished, for example, by providing that the intermediate wall between the large and small lumens terminates about 5–15 mm, preferably 5–12 mm, upstream of the distal end of the probe. This design of the probe is preferred if holes are arranged in the zone of the distal end in the wall of the probe defining the large lumen, said holes connecting the large lumen with the outside air and the holes lying in the combined region of the lumens.

The probe is made of a flexible, pliable and sterilizable material, for example of a synthetic resin, and has a length of about 30–55 cm sufficient for introduction into the bronchi. The diameter of the large lumen for suctioning mucus is about 3–4.5 mm.

For the safe and flawless introduction of the probe into the trachea, it is furthermore suggested that the distal end that can be introduced into the bronchial system be rounded, preferably fashioned with an annular bead projecting on the outside a small extent past the wall of the probe. This provides for a satisfactory guidance of the probe within the trachea. The unilateral projection of the annular bead should not be more than about 0.4 to 1.4 mm, so that the permissible outer diameter of the probe is not exceeded. It is possible to choose the larger projection in case of a smaller outer diameter.

The probe can also be fashioned with lateral holes in the wall of the large lumen in the proximity of the annular bead, i.e., in the distal terminal zone of the probe, preventing an adherence of the probe due to suction to the mucous membranes. These holes need only have a very small diameter of about 1 mm. In some embodiments, the lateral holes can be omitted.

The proximal end of the probe can be connected in the inlet of the large lumen with a connecting piece for a suction device which is, for example, plugged in. For this purpose, the provision is made in an advantageous further development of the probe that, at the proximal end, the wall of the probe and the two lumen inlets, but at least the large lumen inlet, flare conically. The connecting pieces for the suctioning can likewise be fashioned with a valve or a closure means, such as a plug, a sealing cap. Furthermore, the tube wall of the probe can be equipped according to this invention with an X-ray contrast strip in the axial longitudinal extension. This permits X-ray control during the treatment of a patient, and positional control of the probe.

Considerable progress in treating patients is achieved by the invention in the medical field here under consideration. Heretofore, it has merely been possible to proceed in the following sequence during reanimation and emergencies, using the presently available devices:

(1) Introduction of a respirator tube into the trachea.

(2) Introduction of irrigation solution into the respirator tube.

(3) Ventilation with a respirator bag for distributing the irrigation fluid.

(4) Introduction of a suction catheter with exclusive suctioning.

(5) Removal of suction catheter.

(6) Introduction of a cava catheter, incurring the dangers of injury to the mucous membrane (stopgap solution).

(7) Introduction of emergency medicaments via the cava catheter.

(8) Removal of cava catheter.

(9) Initiation of volume-controlled respiration.

The time required for this purpose is, in total, about 3 to 3½ minutes.

With this therapy, damage due to lack of oxygen supply to the patient cannot be excluded. Also, adequate administration of the emergency medicaments through the cava catheter is not always ensured. Additionally, there is the high consumption of material, which requires a lot of labor and is uneconomical.

With the invention it becomes possible to take care of the patient as follows:

(1) Introduction of a respirator tube into the trachea.

(2) Introduction of the double-lumen probe according to this invention, designed as an irrigation and suction catheter, via the windpipe.

(3) Simultaneous irrigation and suctioning of the bronchial tract with the probe, irrigation solution proceeding through the small lumen and suctioning through the large lumen.

(4) Subsequent deep administration of emergency medicaments by means of the probe up into the lung through the small lumen.

(5) Removal of the probe.

(6) Beginning of volume-controlled respiration through the respiration tube.

Duration of the entire treatment is 30 seconds to 1 minute.

By using the invention, a substantially faster and shortened treatment of the patient is made possible, considerably increasing the patient's chances for survival. Damage to the central nervous system can be reduced to an utmost minimum. Moreover, the labor to be performed is substantially less, and this is also true for the utilization of material.

BRIEF DESCRIPTION OF THE DRAWINGS

The invention is explained with reference to the accompanying drawings with the use of examples, but is not limited thereto.

The drawings show, in schematic representation.

DETAILED DESCRIPTION OF THE INVENTION

Figure 1:
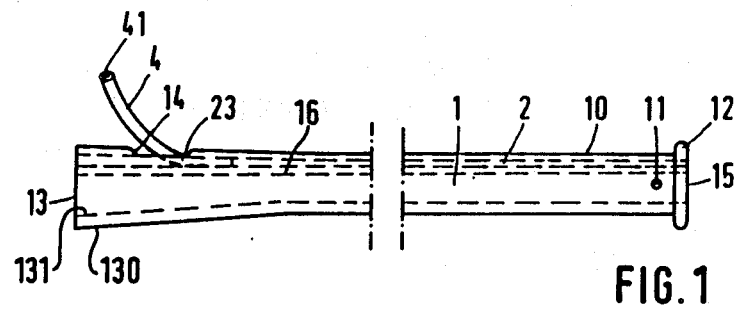
FIG. 1 is a longitudinal side schematic view of a double-lumen probe with dash lines showing the relative locations of the first and second lumens.
Figure 2:
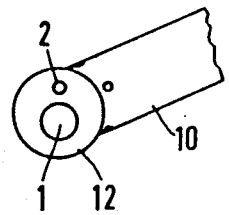
FIG. 2 is a perspective partial plan view of the distal end of the probe according to FIG. 1.
Figure 3:
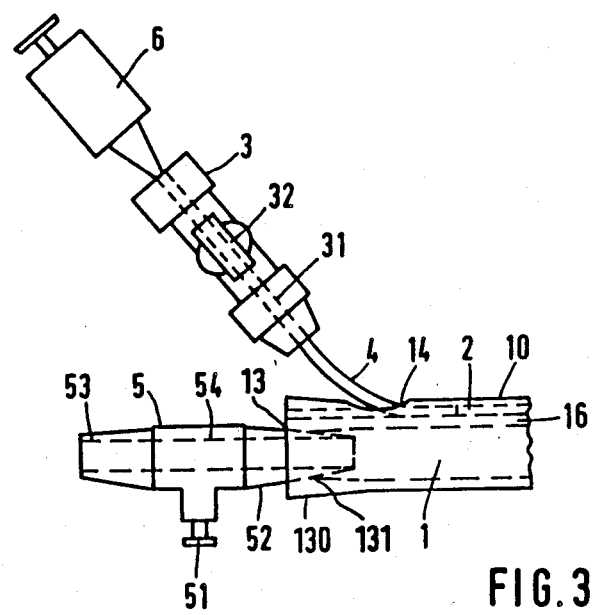
FIG. 3 is a side schematic view of the proximal end of a double-lumen probe.

In FIGS. 1-3, an embodiment of the double-lumen probe 10 is illustrated for the introduction of medicaments into the lung and for suctioning. The tubular probe 10 is manufactured, for example, by extrusion from a thermoplastic synthetic resin and is elastic and pliable. The probe has, for example, an outer diameter of about 7 mm and is fashioned as a unitary cylindrical body with two continuous lumens 1, 2 (i.e., bores or passages) extending in side-by-side relationship in parallel. At the distal end 15 of the probe 10, introducible into the windpipe, an annular bead 12 is formed on the outside, serving for the facilitated introduction of the probe into the windpipe. The probe exhibits, preferably in the region of the distal end upstream of the annular bead 12, holes 11 in the outer wall defining the large lumen 1; these holes are to prevent adhering of the probe 10 to the mucous membranes due to suction. The perspective view of the distal end of the probe 10 according to FIG. 2 shows the arrangement and the flush, side-by-side termination of the two lumens 1, 2 of differing diameters at the distal end. The large lumen 1 extending from the proximal end 13 of the probe to the distal end 15 has a diameter of about 3–5 mm. Through this large lumen 1, secretions, water and mucous or the like are suctioned off from the lung and bronchi. The small lumen 2 extends in parallel to the large lumen 1; these lumens are separated from each other by the partition or wall 16. For reasons of manufacturing technique, the small lumen 2 likewise extends preferably continuously from the proximal to the distal end of the probe. The small lumen 2 has a smaller diameter of about 1 to maximally 2 mm. The small lumen serves for the introduction of medicaments or irrigation solutions into the lung. The probe of FIG. 1 is a double-lumen catheter for intrabronchial suctioning of secretions and administration of medicaments and/or irrigation solutions. For this purpose, the probe 10, which has a length of, for example, 50 cm, is provided with corresponding connections for the small and large lumens 2, 1. The equipment of the probe 10 with connections in the proximal zone is illustrated by way of example in FIG. 3. The proximal end zone of the probe 10 can be fashioned, for example, with a slight conical flare 130 encompassing the lumen inlets, as well as the walls defining same. In this way, the inlet opening 131 of the large lumen forms a conical funnel for the insertion of a connection for a suctioning device.

One possibility for introducing medicament solution or irrigation solution into the small lumen 2 resides in the introduction at the proximal end 13 of the probe directly via a connecting piece into the small lumen 2. A further possibility, preferred according to the invention due to greater freedom in handling, resides in forming the recess 14 in the wall of the probe defining the small lumen, in the region of the proximal end 13 of the probe 10, i.e., with a certain distance from the proximal end. Through this recess 14, a connection, for example, an elastic hose section 4, can be inserted in the inlet 23 of the small lumen and firmly joined therewith. At the end 41, the attachment 3 for the syringe 6 can be connected to the elastic hose section 4, or the attachment can be formed directly integrally at the hose end 41 so that, via the attachment and the hose 4, the medicaments can be introduced into the lumen 2 and thus through the trachea into the lung.

FIG. 3 shows schematically the connection and shapes of connecting pieces 5 for suctioning and of attachments 3 for the syringes 6 of a probe according to FIG. 1. The connecting piece 5, with the conical end 52, is inserted in the conically flaring inlet 131 of the lumen 1 of probe 10. The attachment 5 has the continuous bore 54 which can be sealed by means of the valve 51. For attaching a suctioning device, the connecting piece 5 furthermore comprises the conical tap 53.

For introducing medicaments or irrigation solution by means of a syringe 6 into the lumen 2, the free hose end 4 is equipped with the attachment 3. The attachment 3 has the continuous bore 31 that can be closed by means of a valve 32 designed, for example, as a three-way cock. One end of the attachment 3 is connected to the hose end 4 while, at the other end, the syringe 6 can be introduced into the bore 31. It is also possible to utilize different attachments or devices for this purpose.

The probes constructed in accordance with the invention thus make it possible, in the emergency treatment of human patients, to administer medicaments deeply and safely into the bronchial system and into the lung, and to suction off beforehand, in the same operation, mucus and secretions when the design has lumens that extend in side-by-side relationship in parallel.

With the use of the double-lumen probe according to this invention, the irrigation and suctioning can also be performed with respiration, i.e. without cutting off a respirator unit via the access of a rectangular, dual rotary connector at the tube.

Figure 4:
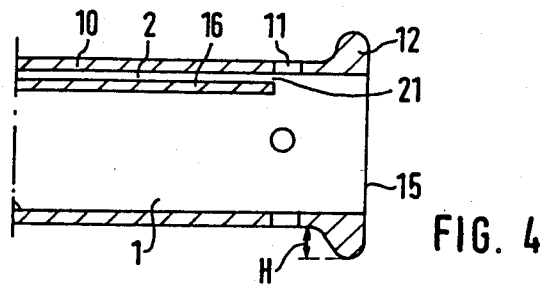
FIG. 4 shows a fragmentary longitudinal section of the distal end of a double-lumen probe with an annular bead.

In FIG. 4, a fragmentary cross-sectional view shows the structure of the distal end 15 of a double-lumen probe exhibiting at the end the annular bead 12 and the holes 11, and wherein the smaller lumen 2 terminates within the probe 10, preferably still upstream of the holes 11, in parallel into the large lumen. The partition 16 between the lumens 1, 2 terminates in this embodiment within the probe 10, but only at a small spacing, covering a few millimeters, i.e., about 5 millimeters, from the distal end 15. The holes 11 can be arranged in the zone not covered by the partition where the lumens are combined, i.e., in an outer wall of the large lumen 1.

Figure 5:
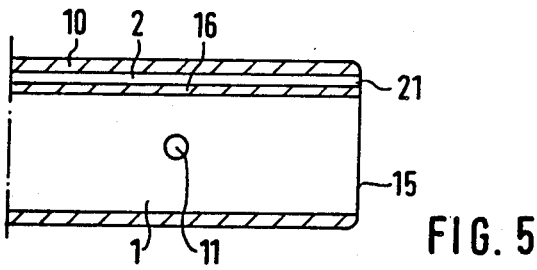
FIGS. 5-8 show, respectively, enlarged fragmentary longitudinal sections of different embodiments of the distal ends of a probe.
Figure 6:
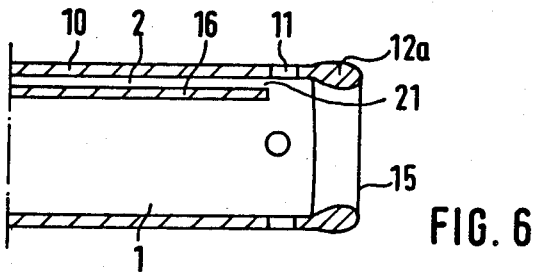
Figure 7:
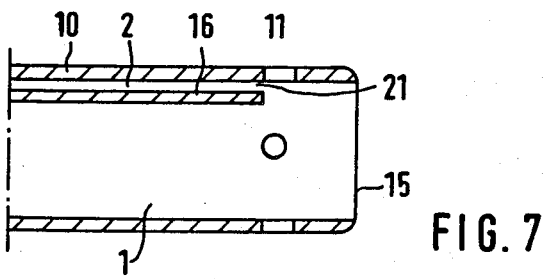

FIGS. 5–7 show additional, advantageous possible embodiments of the distal end zone of the double-lumen probe 10. In the probe according to FIG. 5, the large and small lumens 1, 2 extend side-by-side in parallel, segregated by the partition 16, up to the distal end 15 of the probe 10; the orifice 21 of the small lumen 2 terminates flush with the orifice of the large lumen and the distal end 15. In order to prevent adherence of the probe due to suction and contact with the mucous membranes, at least one hole 11 is provided in the wall of the probe surrounding the large lumen, at a sufficient distance, relatively freely selectable, from the distal end 15 of the probe. The walls of the probe 10 are fashioned preferably to be slightly rounded at the distal end 15. It is also possible to widen the small lumen 2 slightly in a nozzle shape in the orifice zone 21 in order to promote distribution of the introduced medicaments.

Figure 8:
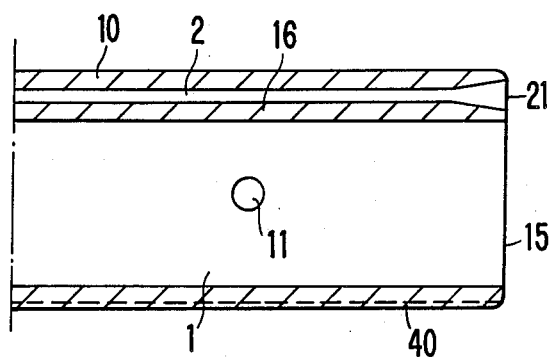

In the embodiment of the distal end zone of the probe 10 as shown in FIG. 6, the rounding of the probe end, i.e. of the outer wall, is obtained by a small thickened portion extending inwardly, thus stabilizing the probe end, see thickened portion 12a. For this case, it is likewise advantageous to have the partition 16 between the small and large lumens 2, 1 terminate a few millimeters, up to about 1 cm, upstream of the distal end 15 so that the small lumen 2 and the large lumen 1 terminate in parallel side-by-side relationship still within the probe end and exit jointly together from the distal end 15. The holes 11 for preventing adherence by suction to the mucous membranes can here be arranged in the zone of the distal end region devoid of the partition 16, all around the large lumen in uniform fashion, for example, by twos, threes or fours. In FIG. 7, an embodiment of a distal end zone of the probe 10 as in FIG. 6 is illustrated, but without a thickened end of the wall at the distal end 15 of the probe. In FIG. 8 an embodiment of the distal end of the body of the probe is illustrated with an enlarged outlet 21 of the lumen 2 and with an x-ray contrast strip 40 provided in the outer wall.

What is claimed is:

1. A tubular flexible probe said probe comprising a unitary body means for introduction into the trachea and, respectively, into the bronchial system having a longitudinal axis, a proximal end, a distal end and an outer wall, said outer wall defining a cylindrical portion at the distal end extending to and integrally joined with a conically flared portion at the proximal end, said body means being made of a synthetic resin and containing a continuous first lumen means for suctioning and a continuous second lumen means for administration of fluid media having a smaller diameter than the first lumen means, said unitary body means further including an inner partition wall separating the first lumen means and said second lumen means the outer wall of the body means having a recess extending through said outer wall into the second lumen means, said recess being adjacent to the proximal end of the body means; an elastic connecting hose having two ends, one of the ends defining an inlet and the other end being inserted via said recess into the second lumen means and joined thereto; said first lumen means and said second lumen means extending from the proximal end of the body means to at least a zone adjacent to the distal end of the body means in side-by-side relationship and in parallel to the longitudinal axis of the body means and at least the first lumen means terminating at the distal end of the body means; and the exterior of the distal end of the body means having a round configured means whereby introduction of fluid media into the second lumen means and suctioning of fluids including secretions through the first lumen means can be effected alternatingly and whereby a high exit velocity of the fluid media introduced into the second lumen means is provided at the distal end of the body means; said probe having the following characteristic features:
  (a) the body means has a length of about 30–55 cm,
  (b) the outer wall of the body means has a diameter of about 5–8 mm,
  (c) the first lumen means has an inner diameter of about 3–4.5 mm,
  (d) the second lumen means has an inner diameter of about 1 to maximally 2 mm, and
  (e) attachment means at the inlet end of the connecting hose providing a fitting for a syringe.

2. A probe according to claim 1, wherein the diameter of the second lumen means amounts to about 1 to 1½ mm.

3. A probe according to claim 1, wherein the rounded configured means comprises an annular bead slightly projecting from the outer wall encompassing the lumen means.

4. A probe according to claim 3, wherein the projection of the annular bead is about 0.4 to 1.4 mm.

5. A probe according to claim 1, wherein the attachment means for the syringe is fashioned integrally with the connecting hose.

6. A probe according to claim 1, wherein the attachment means for the syringe suctioning lumen is equipped with a closure means.

7. A probe according to claim 1, wherein the outer wall is equipped, with an X-ray contrast strip along the longitudinal axis.

8. A probe according to claim 1, wherein the partition wall separating the two lumen means from each other terminates within the body means shortly upstream of the distal end.

9. A probe according to claim 8, wherein the partition wall terminates about 5 mm to 12 mm upstream of the distal end.

10. A probe according to claim 12, wherein the second lumen means has an outlet at the distal end which is widened in the manner of a nozzle.

11. A probe according to claim 12, wherein at the proximal end, the conically flared portion of the outer wall defines the inlet of the first lumen means which is conically widened to allow insertion of a suction device into the inlet of said first lumen means.

12. A probe according to claim 11, further comprising a connecting means for connection to the suction device, said connecting means being inserted into the inlet of said first lumen means.

13. A probe according to claim 1, wherein said body means further includes in a zone adjacent to the distal end at least one penetrating hole provided in a portion of the outer wall defining a wall of the first lumen means.

14. A probe according to claim 13, wherein the outer wall provides a continuous non-perforated surface extending from the recess to the at least one penetrating hole so that discharge of the fluid media and suctioning occurs alternatingly only at the distal end.

* * * * *